US00PP12706P2

(12) United States Plant Patent
Kaskel

(10) Patent No.: US PP12,706 P2
(45) Date of Patent: Jun. 18, 2002

(54) HEMEROCALLIS PLANT NAMED 'PIPER MITCHELL'

(75) Inventor: Mathew Kaskel, Homestead, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/657,544

(22) Filed: Sep. 8, 2000

(51) Int. Cl.[7] ..... A01H 5/00
(52) U.S. Cl. ..... Plt./312
(58) Field of Search ..... Plt./312

*Primary Examiner*—Bruce R. Campell
*Assistant Examiner*—June Hwu
(74) *Attorney, Agent, or Firm*—Foley & Lardner

(57) ABSTRACT

A new cultivar of Hemerocallis plant named 'Piper Mitchell' characterized by its large yellow flowers tinged with orange which are borne on short branched scapes. The flowers do not fade in warm, bright conditions and are resistant to water spotting. Plants of 'Piper Mitchell' bloom very early in the season, and then repeatedly through out the growing season. Plants of 'Piper Mitchell' are evergreen, thus they are attractive in landscapes. The plant grows vigorously, and propagates easily by division or tissue culture.

2 Drawing Sheets

BACKGROUND OF THE INVENTION

The present invention comprises a new and distinct cultivar of Hemerocallis plant, hereinafter referred to by the cultivar name 'Piper Mitchell'. The genus Hemerocallis is a member of the family Liliaceae.

Hemerocallis comprises a genus of approximately 15 species of clump-forming, herbaceous perennials which are native to central Europe, China, and particularly, Japan. The flowers of Hemerocallis are lily-like and are borne in succession atop tall, frequently-branched scapes. Individual flowers last one day. Thus, Hemerocallis is commonly known as "Daylily" in commercial trade.

In recent years, Hemerocallis has been extensively hydridized, and many cultivars exist. Hemerocallis hybrids are hardy spring- and summer-blooming plants which are particularly well-adapted to landscape plantings.

The plants form clumps of fan-shaped crowns of vertically-ranked, keeled, strap-like leaves. Plants (individual crowns) range in size from approximately 20 cm to over 90 cm in spread. Depending upon the parentage, Hemerocallis hydrids may be deciduous, evergreen or semi-evergreen.

Hemerocallis hybrids come in a range of colors including orange, yellow, pink, reddish or purplish. The flowers are funnel-shaped or campanulate with six segments joined at the base into a tube.

Asexual propagation of Hemerocallis is frequently done by division. Propagation can also be done through the use of tissue culture practices.

The new cultivar 'Piper Mitchell' is a product of a planned breeding program and was originated by the inventor, Matthew Kaskel, from a cross made during such a program in Homestead, Fla. in April of 1991. The male or pollen parent is a selected, unnamed Hemerocallis×hybrid seedling (unpatented) and the female parent is Hemerocallis 'My Darling Clementine' (unpatented). Both parental cultivars are proprietary Hemerocallis selections designated by number codes which are maintained by the inventor and used for breeding purposes only. The selection comprising the new variety was chosen after commencement of flowering of the progeny in April of 1992 and was originally identified by the number code #92-63. After more thorough commercial evaluation, the cultivar was given the name 'Piper Mitchell'.

Asexual propagation of the new cultivar by tissue culture in the laboratories of Twyford Plant Laboratories, Inc., in Homestead, Fla., by the inventor has demonstrated that the combination of characteristics as herein disclosed for the new cultivar 'Piper Mitchell' are firmly fixed, reproduce true to type, and are retained through successive generations of asexual reproduction.

BRIEF DESCRIPTION OF THE DRAWINGS

The accompanying color photographic illustrations show typical characteristics of Hemerocallis 'Piper Mitchell', with colors being as nearly true as possible with illustrations of this type.

Sheet 1 shows a 10-month-old plant of 'Piper Mitchell' grown from tissue culture and flowering in a landscape setting.

Sheet 2 is a close-up view showing the characteristics of the flowers and scape.

DETAILED DESCRIPTION OF THE NEW VARIETY

The following observations, measurements and values describe 10 month old plants derived from a tissue culture plantlet grown in Apopka, Fla., under landscape conditions which closely approximate those generally used in horticultural practice. Color references are made to The Royal Horticultural Society (R.H.S.) Colour Chart, except where general color terms of ordinary significance are used.

The following traits have been repeatedly observed and are determined to be basic characteristics of 'Piper Mitchell' which in combination distinguish this Hemerocallis as a new and distinct cultivar:

1. The flowers are yellow tinged with orange and are large and thick-textured;
2. The flowers do not fade in warm, bright conditions and are resistant to water spotting;

3. Individual scapes are short and balanced with many buds which open in succession for approximately 4 weeks;
4. Spent flowers shrivel, become inconspicuous, drop from the scape quickly, and do not interfere with the opening of subsequent flowers;
5. Plants begin blooming very early in the season (March–April) and rebloom throughout a 90-day blooming season;
6. Plants grow vigorously and propagate readily by division and tissue culture; and
7. Plants have evergreen foliage making them attractive in landscapes even when not in bloom.

'Piper Mitchell' not been observed under all available environmental conditions. The phenotype of the new cultivar may vary significantly with variations in environment such as temperature, light intensity, daylength and humidity without, however, any change in genotype.

In comparison to its female parent 'My Darling Clementine', 'Piper Mitchell' is slightly smaller and sometimes has a slight pink blush which is most noticeable in noticeable in the morning when the buds first open. 'Piper Mitchell' is considerably more cold hardy, and a more productive performer in northern gardens than 'My Darling Clementine'. The male pollen parent is a small cream colored flower, bearing little resemblance to 'Piper Mitchell'.

Classification: Commercial: Hemerocallis cv. 'Piper Mitchell' Genus/Species: Hemerocallis×hybrid.

Parentage:

*Male parent.*—Unnamed proprietary selection of Hemerocallis.

*Female parent.*—Proprietary selection of Hemerocallis named 'My Darling Clementine'.

Propagation: Vegetative, by crown division.

Plant:

*Form/growth habit.*—Clump-forming; fan-shaped crowns of vertically ranked, opposite, smooth, keeled, ligulate leaves.

*Height.*—Approximately 38 cm to 41 cm including inflorescence.

*Width.*—Approximately 48 cm to 53 cm.

Foliage:

*Size.*—Mature leaves are approximately 45 cm to 55 cm long and 2.9 cm wide.

*Shape.*—The leaf blade is ligulate with an acute tip. The margins are entire. The leaves are curved over their length. The leaf is keeled and arched downward.

*Surface texture.*—The leaf blade is relatively thin with a smooth surface.

*Color.*—The leaves are medium green throughout. The upper surfaces are greener than, but closest to 137 B, and lower surfaces are 137 C.

*Average number.*—The plant produces approximately 7 pairs of leaves before producing an inflorescence.

*Dormancy.*—Plants are evergreen, and require no dormant period. If grown in appropriate conditions, plants of 'Piper Mitchell' are capable of growing year round.

Inflorescence:

*Borne.*—Flowers borne in succession, with new buds opening daily, atop a 2 or 3 branched scape. Scapes may produce approximately 10–12 buds, with each branch having 3–4 buds each.

*Shape.*—Upright terminally branched determinant panicle bearing 10–12 flowers which open daily in succession.

*Buds.*—Dimensions: Approximately 6.3 cm long and 1.9 cm in width. Color: Basically green 145 A, 146 C becoming yellower than, but closest to between RHS 150 C and RHS 150 D before opening.

*Individual flowers.*—Dimension: The diameter of the flower is approximately 10.5 cm to 11.5 cm (not flattened). The flower depth is 6.0 to 7.0 cm. The sepals are approximately 8 cm long 4 cm wide, and are elliptic in shape. The petals are approximately 7.5 cm long, 5.9 cm wide, and are broadly elliptic in shape.

*Shape.*—Funnel-form to campanulate, segments elliptic and moderately reflexed. The three petals are distinctly ruffled along the margins. The three sepals are distinctly wavy along the margins. The petal and sepal apex shape is cuspidate.

*Colors.*—Upper surface: Sepals yellow RHS 9 C, flushed with RHS 25 D in center. Base of sepal between RHS 145 B and RHS 145 C. Petals yellow between RHS 9 A and RHS 9 B, flushed with RHS 25 D in center. Base of petals (Throat): RHS 144 C. Lower Surface: Yellow RHS 9 D marginally, between RHS 9 B and RHS 9 C flushed with RHS 145 B. Base of Sepal: between RHS 145 B and RHS 145 C. Tip of Sepal: RHS 144 B. Petals yellow between RHS 9 B and RHS 9 C, flushed with RHS 25 D in center. Base of petals: flushed with RHS 144 C. Texture: Moderately thick, leathery texture. Quantity: Approximately 10–12 flowers/buds present depending on the size of plant and inflorescence. Branch spikes contain approximately 3 to 4 flowers/buds. Senescent flower: Spent flowers collapse and shrivel, becoming inconspicuous, eventually falling from the scape in 1 or 2 days. Scape: The scape is approximately 38 cm to 41 cm in height, and 1 cm in diameter measured at midpoint and darker than, but closest to between RHS 146 A and RHS 146 B in color. Bracts: Small leaf-like bracts are present at the junctions of the branches and the scape and the flower buds and the scape. The bracts are variable in size, 1.5 cm to 5.2 cm long and are between RHS 146 B and RHS 146 C in color both upper and lower surfaces. Time of blooming: In mature plants, flowering begins approximately very early season (March 15 as observed in Apopka, Fla.). Duration of blooms: Individual flowers last 1 day, and the total duration of flowering is about 90 days with subsequent scapes appearing through out the growing season. Fragrance: Slight.

Reproductive organs:

*Ovary.*—Superior oblong, 8 mm in length, 6 mm wide. Color: 146 C.

*Pistil.*—1 per flower, 9.3 cm long, style 2.0 mm wide, between RHS 14 C and RHS 14 D, and RHS 18 A in color.

*Stamens.*—Six present, Filament 3.9 cm long, flat curved 2 mm wide, color 11 B.

*Anthers.*—9 mm long, 11 B in color.

*Pollen.*—Color — 21 A.

Seed characteristics: Capable of producing viable seed , 3 to 6 shiny black seeds per chamber, 4 mm to 6 mm, mostly round, often oblong, variably shaped.

Fruit characteristics: 3 valved, loculicidal capsule, 2.5 cm wide and 3.2 cm long, color RHS 137 B, becoming tinged with yellow, RHS 20 C when ripe.

Roots: Very thick fleshy white roots with fine laterals.

Cultural:

*USDA zone.*—Grows and blooms best when grown in USDA Zones 4 to 11.

Diseases/pests: No particular sensitivity to pests or diseases. Aphids may infest plants during the winter months.

We claim:

1. A new and distinct cultivar of Hemerocallis plant named 'Piper Mitchell' as illustrated and described.

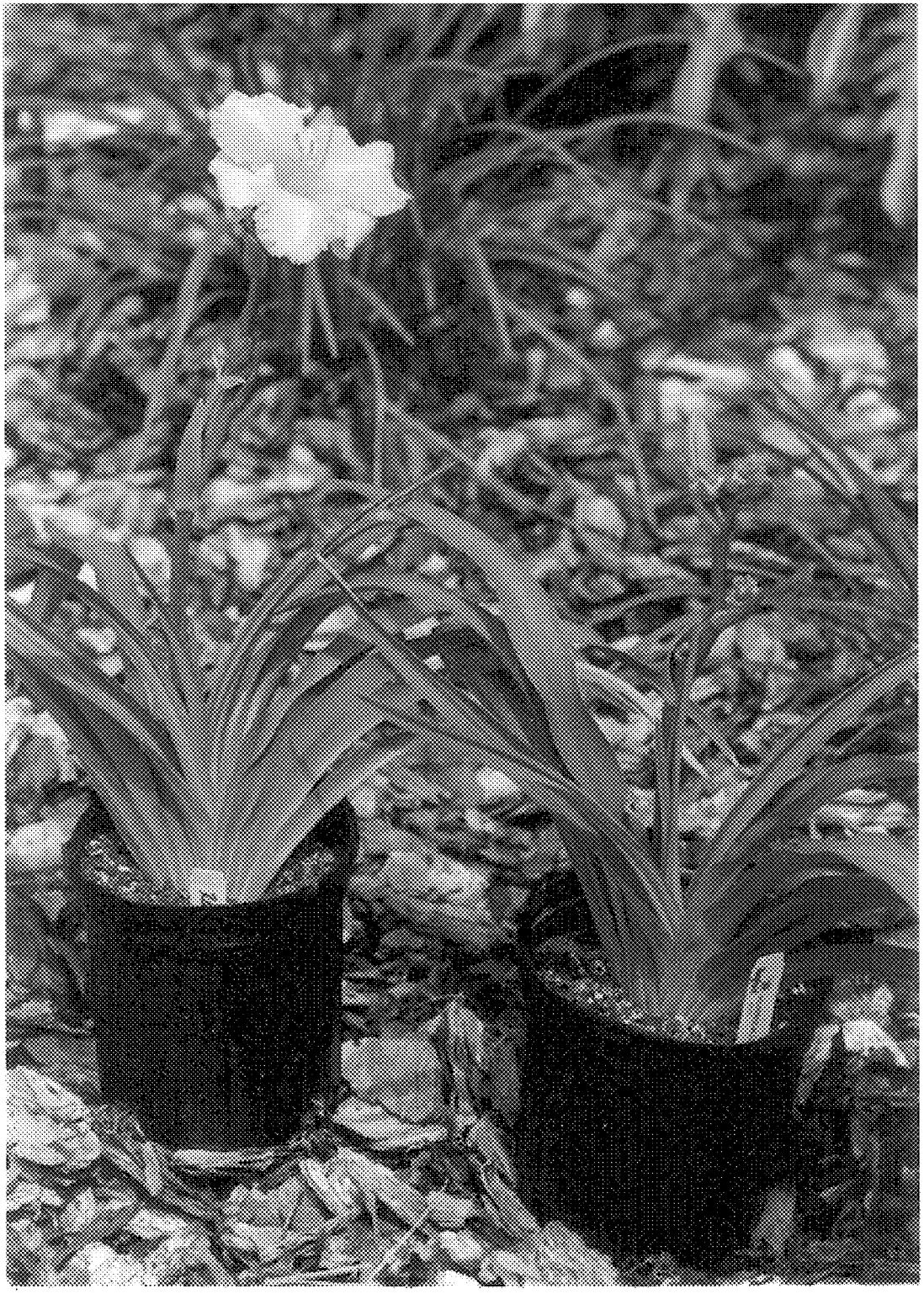

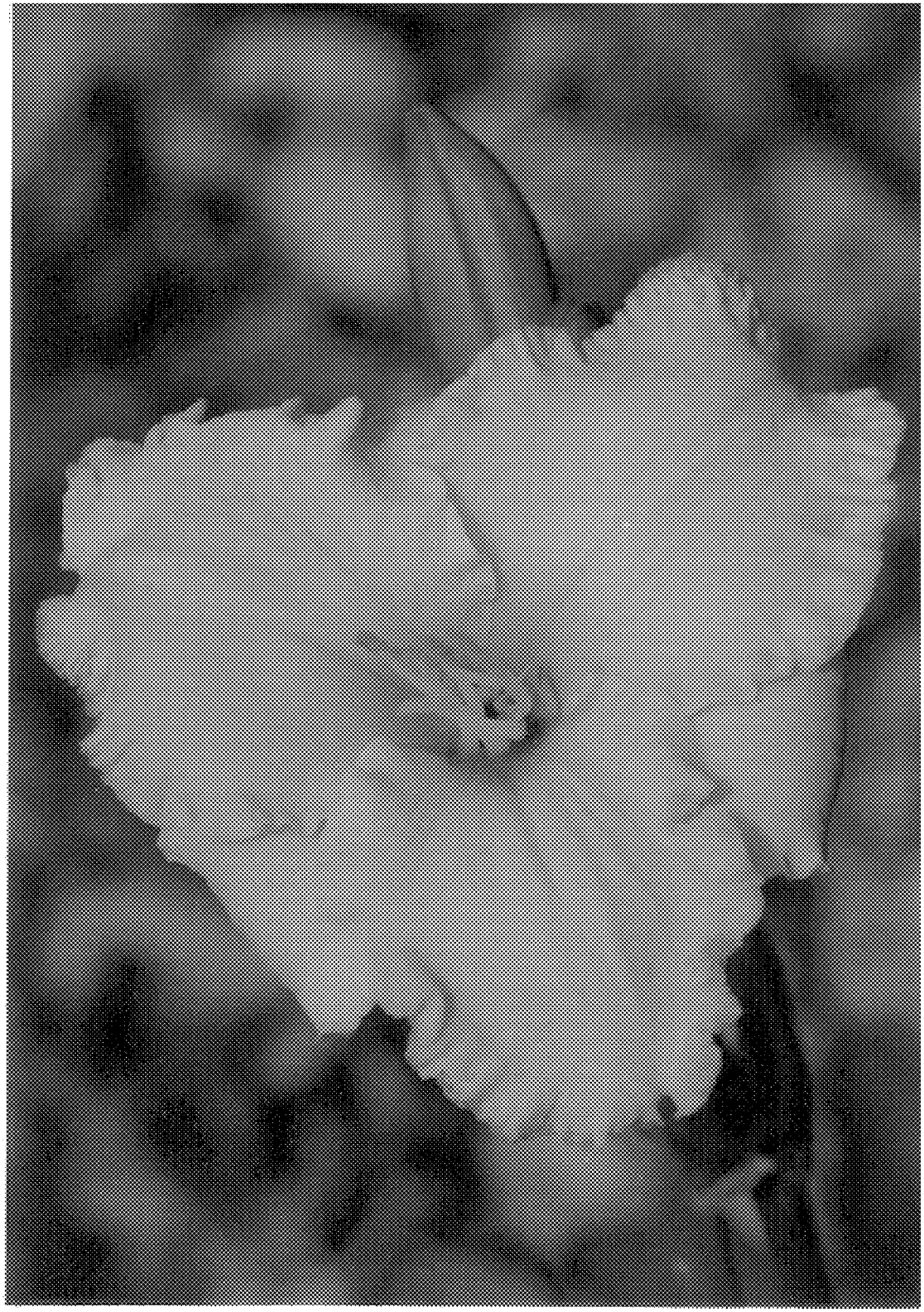

* * * * *